(12) United States Patent
Grim et al.

(10) Patent No.: US 10,716,695 B2
(45) Date of Patent: Jul. 21, 2020

(54) FLEXIBLE ANATOMICAL SUPPORT

(71) Applicant: ORTHO SYSTEMS, Agoura Hills, CA (US)

(72) Inventors: Tracy E. Grim, Agoura Hills, CA (US); Joseph Michael Iglesias, Agoura Hills, CA (US); Eric Gerald Scott, Agoura Hills, CA (US); Justina-Delia A. Franco, Agoura Hills, CA (US)

(73) Assignee: Ortho Systems, Agoura Hills, CA (US)

( * ) Notice: Subject to any disclaimer, the term of this patent is extended or adjusted under 35 U.S.C. 154(b) by 338 days.

(21) Appl. No.: 15/676,953

(22) Filed: Aug. 14, 2017

(65) Prior Publication Data

US 2017/0340470 A1 Nov. 30, 2017

Related U.S. Application Data

(60) Division of application No. 13/421,745, filed on Mar. 15, 2012, now abandoned, which is a continuation of application No. PCT/US2011/046226, filed on Aug. 2, 2011, which is a continuation of application No. 13/195,767, filed on Aug. 1, 2011, now abandoned.

(60) Provisional application No. 61/369,921, filed on Aug. 2, 2010.

(51) Int. Cl.
  *A61F 5/01* (2006.01)
(52) U.S. Cl.
  CPC .................... *A61F 5/0118* (2013.01)
(58) Field of Classification Search
  CPC .......................................................... A61F 5/01

USPC ......... 602/21, 20, 5, 1, 22, 64; 2/16, 20, 21, 2/160, 161.1, 161.5, 161.6, 163; 128/878, 128/879, 880, 889

See application file for complete search history.

(56) References Cited

U.S. PATENT DOCUMENTS

| | | |
|---|---|---|
| 3,327,703 A | 6/1967 | Gamm |
| 4,193,135 A | 3/1980 | Rhee |
| 4,438,532 A | 3/1984 | Campanella et al. |
| 4,561,122 A | 12/1985 | Stanley et al. |
| 4,709,694 A | 12/1987 | O'Connell |
| 4,779,289 A | 10/1988 | Prouty |
| 4,840,168 A | 6/1989 | Lonardo |
| 4,852,557 A | 8/1989 | Grim |
| 4,893,616 A | 1/1990 | Gibaud |
| 4,964,402 A | 10/1990 | Grim et al. |
| 4,996,979 A | 3/1991 | Grim et al. |

(Continued)

FOREIGN PATENT DOCUMENTS

| | | |
|---|---|---|
| EP | 2453849 A1 | 5/2012 |
| JP | 2003522594 A | 7/2003 |

(Continued)

OTHER PUBLICATIONS

International Preliminary Report on Patentability dated Feb. 5, 2013 and Written Opinion dated Nov. 25, 2011 re PCT/US2011/046226.

(Continued)

*Primary Examiner* — Tarla R Patel
(74) *Attorney, Agent, or Firm* — Fulwider Patton LLP

(57) ABSTRACT

A flexible support including a body configured to provide anatomical support to a user's appendage, and an insert extending along at least a portion of an edge of the flexible support to reduce irritation and fitment discomfort to the user's appendage from the edge.

2 Claims, 14 Drawing Sheets

(56) References Cited

U.S. PATENT DOCUMENTS

| | | | |
|---|---|---|---|
| 5,014,689 A | 5/1991 | Meunchen et al. | |
| 5,058,576 A | 10/1991 | Grim et al. | |
| 5,445,602 A | 8/1995 | Grim et al. | |
| 5,551,950 A | 9/1996 | Oppen | |
| 5,572,738 A | 11/1996 | Melone, Jr. | |
| 5,675,839 A | 10/1997 | Gordon et al. | |
| 5,713,837 A * | 2/1998 | Grim | A61F 5/0111 602/21 |
| 5,772,619 A | 6/1998 | Corbett | |
| 5,836,902 A | 11/1998 | Gray | |
| 5,925,010 A | 7/1999 | Caprio, Jr. | |
| 5,971,946 A | 10/1999 | Quinn et al. | |
| 5,980,476 A | 11/1999 | Wiederrich | |
| 1,627,382 A | 7/2000 | Golomb | |
| 6,085,354 A | 7/2000 | Wilder et al. | |
| 6,126,625 A | 10/2000 | Lundberg | |
| 6,279,159 B1 | 8/2001 | Ahlbaumer et al. | |
| 6,482,167 B2 | 11/2002 | Grim et al. | |
| 6,496,984 B1 | 12/2002 | Chow | |
| 6,572,571 B2 | 6/2003 | Lowe | |
| 6,691,315 B1 | 2/2004 | Clarke et al. | |
| 6,702,772 B1 * | 3/2004 | Colditz | A61F 5/0118 602/20 |
| 6,721,960 B1 | 4/2004 | Levesque et al. | |
| 7,056,298 B1 * | 6/2006 | Weber | A61F 5/0118 2/16 |
| 7,311,686 B1 * | 12/2007 | Iglesias | A61F 5/0111 602/20 |
| 7,469,426 B2 | 12/2008 | Roeckl | |
| 8,114,041 B2 * | 2/2012 | Wyatt | A61F 5/0118 128/846 |
| 8,312,563 B1 * | 11/2012 | Burns | A41D 19/01 2/16 |
| 8,657,771 B2 * | 2/2014 | Weaver, II | A61F 5/0118 602/20 |
| 2005/0121562 A1 | 6/2005 | Baumgardner | |
| 2005/0273030 A1 * | 12/2005 | Koby | A61F 5/0118 602/60 |
| 2007/0100266 A1 * | 5/2007 | Hargrave | A61F 5/0118 602/21 |
| 2007/0157364 A1 * | 7/2007 | Comstock | A63B 71/141 2/161.1 |
| 2007/0225630 A1 | 9/2007 | Wyatt et al. | |
| 2008/0319362 A1 | 12/2008 | Joseph | |
| 2009/0012438 A1 | 1/2009 | Frangi | |
| 2010/0094189 A1 | 4/2010 | Ingimundarson et al. | |
| 2011/0066095 A1 | 3/2011 | Price et al. | |
| 2011/0146032 A1 | 6/2011 | Hu et al. | |

FOREIGN PATENT DOCUMENTS

| | | |
|---|---|---|
| JP | 2004533286 A | 11/2004 |
| JP | 2009513262 | 4/2009 |
| WO | WO1992019196 A1 | 11/1992 |
| WO | WO1995031950 A1 | 11/1995 |
| WO | WO2001060289 A1 | 8/2001 |
| WO | WO20020217827 A1 | 3/2002 |
| WO | WO2002078579 A1 | 10/2002 |
| WO | WO2006084220 A2 | 8/2006 |
| WO | WO2007050703 A2 | 5/2007 |
| WO | WO2011007103 A1 | 1/2011 |

OTHER PUBLICATIONS

International Search Report—PCT/US2011046226, International Search Authority—European Patent Office dated Nov. 25, 2011.
Japanese Office Action dated May 25, 2015, regarding Japan Application No. JP2013-523265.
Japan Decision for Refusal dated Nov. 2, 2015, regarding Japanese Application No. 2013-523265 and English translation.
First Office Action dated May 19, 2014, regarding Australian Patent Application No. AU2011285940.
Second Australian Office Action dated Apr. 19, 2015, regarding Australian Application AU2011285940.
Third Australian Office Action dated Sep. 3, 2015, regarding Australian Application No. 2011285940.
EP Communication dated May 10, 2017 and Annex attached, regarding EP11815168.7.
EP Communication dated Dec. 5, 2014 and Annex attached, regarding EP11815168.7.
First Office Action dated Oct. 3, 2016, regarding Australian Patent Application No. AU2016200934.
Second Office Action dated Sep. 6, 2017, regarding Australian Patent Application No. AU2016200934.

* cited by examiner

US 10,716,695 B2

FLEXIBLE ANATOMICAL SUPPORT

CROSS-REFERENCE TO RELATED APPLICATION

This present application is a divisional of, and claims priority to, U.S. patent application Ser. No. 13/421,745, filed Mar. 15, 2012, entitled "FLEXIBLE ANATOMICAL SUPPORT," now pending, which application is a continuation of International Patent Application No. PCT/US2011/046226, filed Aug. 2, 2011, entitled "FLEXIBLE ANATOMICAL SUPPORT, which application in turn claims priority to U.S. patent application Ser. No. 13/195,767, filed Aug. 1, 2011, abandoned, and to U.S. Provisional Application Ser. No. 61/369,921, filed Aug. 2, 2010, the contents of each of which are expressly incorporated herein by reference in their entirety as if fully set forth herein.

BACKGROUND

Field

The present disclosure relate generally to flexible anatomical supports, and more particularly, to a flexible support that includes a cushioning material to reduce irritation and fitment discomfort to a user's appendage.

Background

A flexible support, such as a wrist brace is used to provide compression and support for wrist, hand and forearm for management of post fracture or soft tissue injuries and other conditions. The thumb protrudes through a thumbhole to allow function of the thumb. The hand and fingers extend from the distal portion of the brace and allow for the most part 90° flexion at the metacarpal phalangeal (MP) Joint. Typically, a liner fabric covers the interior of the brace to provide some comfort where skin contact is made. For the most part, there is restricted motion between the brace and most of the hand. However, thumb motion may lead to irritation of the skin where the thumb crosses over the web space of the wrist brace during pitching motion, and most especially at stitching (binding) around the edge of the thumbhole where layers of material are sewn together. It may also have friction at MP joint of hand at the palmar crease. It is desirable to amend the structure of the brace in this and other locations to provide added cushioning and reduce skin irritation from friction due to hand/finger motion during use of hand while wearing. Particularly when the hand is tender, swollen from injuries, and/or pathological conditions. Preferably, the concepts for amending the structure should be applicable to other flexible supports.

SUMMARY

In an aspect of the present invention, a flexible support includes a body configured to provide anatomical support to a user's appendage, and a cushioning material extending along at least a portion of an edge of the flexible support to reduce irritation and fitment discomfort to the user's appendage from the edge.

In another aspect of the present invention, a brace assembly includes a brace configured to restrict movement of a user's appendage, the brace having a through hole defined by an inner edge, and an insert extending along at least a portion of the inner edge of the brace to reduce irritation and fitment discomfort to the user's appendage from the edge. The insert may include a perforated pad attached to an interior surface of the brace.

In another aspect of the present invention, a flexible support includes a body configured to provide anatomical support to a user's appendage, and means, extending along at least a portion of an edge of the flexible support, for reducing irritation and fitment discomfort to the user's appendage from the edge.

It is understood that other aspects of the present invention will become readily apparent to those skilled in the art from the following detailed description, wherein it is shown and described only exemplary configurations of a flexible support by way of illustration. As will be realized, the present invention includes other and different aspects of a flexible support and its several details are capable of modification in various other respects, all without departing from the spirit and scope of the present invention. Accordingly, the drawings and the detailed description are to be regarded as illustrative in nature and not as restrictive.

BRIEF DESCRIPTION OF THE DRAWINGS

Various aspects of the present invention are illustrated by way of example, and not by way of limitation, in the accompanying drawings, wherein.

DETAILED DESCRIPTION

Figure 1A:
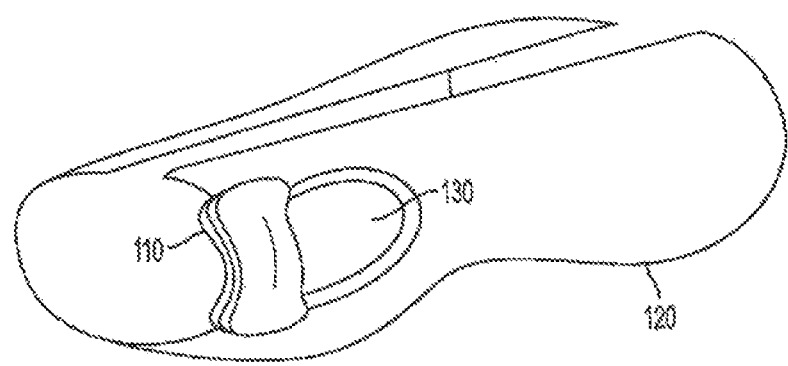
FIG. 1A shows a perspective view illustrating an example of an insert attached to a brace.

The present invention is described more fully hereinafter with reference to the accompanying drawings, in which various aspects of the present invention are shown. This invention, however, may be embodied in many different forms and should not be construed as limited to the various aspects of the present invention presented throughout this disclosure. Rather, these aspects are provided so that this disclosure will be thorough and complete, and will fully convey the scope of the present invention to those skilled in the art. The various aspects of the present invention illustrated in the drawings may not be drawn to scale. Rather, the dimensions of the various features may be expanded or reduced for clarity. In addition, some of the drawings may be simplified for clarity. Thus, the drawings may not depict all of the components of a given apparatus or method.

Various aspects of a wrist brace will now be presented. However, as those skilled in the art will readily appreciate, these aspects may be extended to other flexible supports without departing from the spirit and scope of the invention. More specifically, the various aspects of a wrist brace presented throughout this disclosure are applicable to any suitable flexible support providing anatomical support to any appendage, including by way of example, braces or supports for the foot, ankle, knee, leg, or any other suitable appendage. Various inserts for use with a flexible support are disclosed. For the purposes of this disclosure, an "insert" is a material formed with the flexible support to reduce irritation and fitment discomfort to the user. The insert may be integrally formed with the flexible support or manufactured separately for attachment to a flexible support. The various concepts presented throughout this disclosure are well suited for wrist braces to provide cushioning and comfort in regions of the hand where know irritation and discomfort arise due to contact with the brace, whether the fingers and palm are static or dynamically free to move, and lack of air circulation. However, as those skilled in the art will readily appreciate, these concepts are not limited to wrist braces.

FIG. 1A shows an example of an insert 110 attached to a brace 120. Insert 110 includes a material that is softer and more flexible than the materials from which the brace 120 is made, which includes support stays and edge binding. In one example, as shown in FIG. 1A, the insert 110 is applied to a portion of the brace forming a thumbhole 130 to provide cushioning in a portion of the hand web region between the thumb and the index finger, where irritation is a known issue due to rubbing between the brace material and the skin.

Figure 1B:
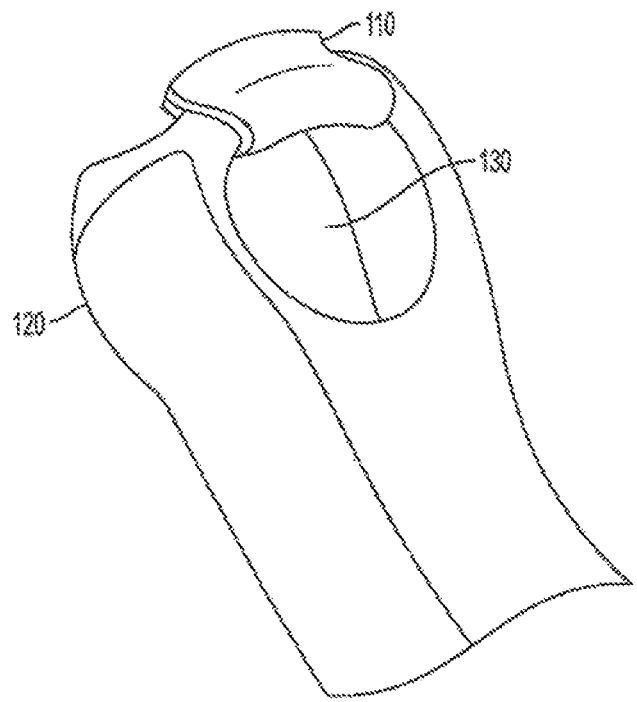
FIG. 1B shows another perspective view of FIG. 1A.

FIG. 1B shows a detail view illustrating an example of the insert 110. The insert 110 may be shaped to a portion of the brace 120 to which it is applied, and may be attached to the brace using a variety of attachment means, including stitching, adhesives, such as glues, fabric hook and loop fasteners, such as Velcro™, and the like.

The insert 110 may comprise one or more layers of one or more different materials. In an embodiment, the insert 110 may be an integral component of the brace 120, and be attached to the brace in the thumb and web space areas of the hand. In another embodiment, the insert may be supplied independent of the brace and attached to the brace in the thumb and web space areas of the hand using any of a variety of adhesive and/or bonding methods.

Figure 2A:
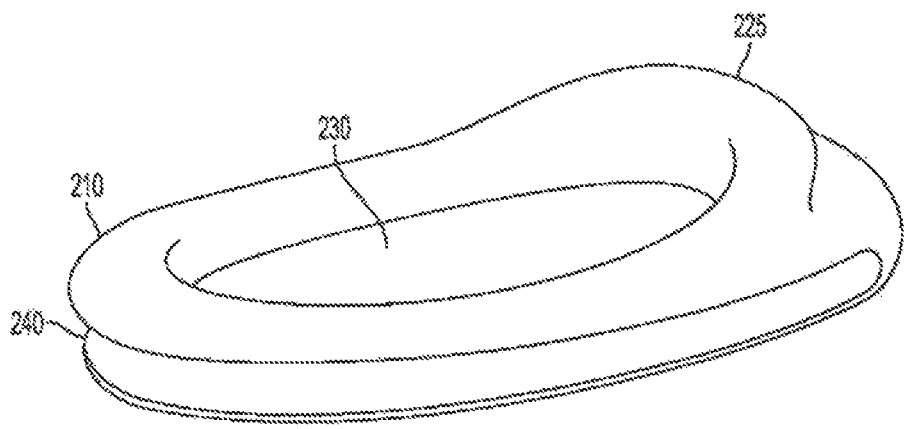
FIG. 2A shows a perspective view illustrating an example of a donut-shaped insert in accordance with the disclosure.
Figure 2B:
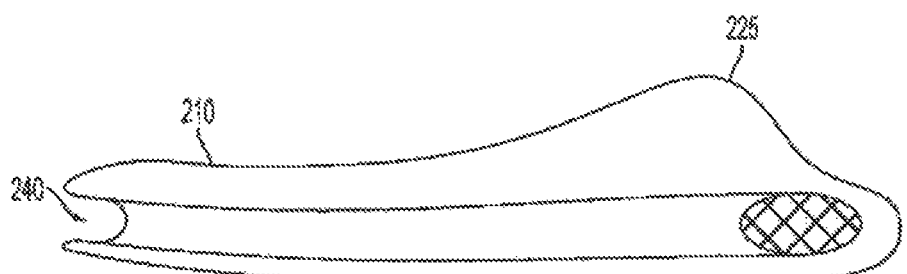
FIG. 2B shows a perspective side-view of the donut-shaped insert of FIG. 2A.

The insert 110 may have various shapes, depending on the customized need or preference of the user. FIG. 2A shows a perspective view illustrating an example of a "donut" insert 210. FIG. 2B shows a side-view illustrating an example of the donut insert 210. The donut insert 210 is approximately ring shaped to fit into the thumbhole 130, and has a corresponding insert thumbhole 230. The donut insert 210 is preferably molded and may have a contoured shape, such as a ridge 225, to provide added cushion at the base of the thumb adjacent to the web of the hand. The donut insert 210 may further have a groove 240 to facilitate insertion and alignment with an interior edge of the thumbhole 130. If the brace 120 includes a bridge across the hand web from the front to back of the hand, that is, if the thumbhole 130 is a complete circle around the thumb, the groove 240 may completely encircle the donut insert 210 to contact the entire thumbhole 130. If the thumbhole 130 is only a partial circle and open in the web area, the groove 240 may be molded to not fully encircle the donut insert 210, but provide extra cushioning material in the web area.

Figure 2C:
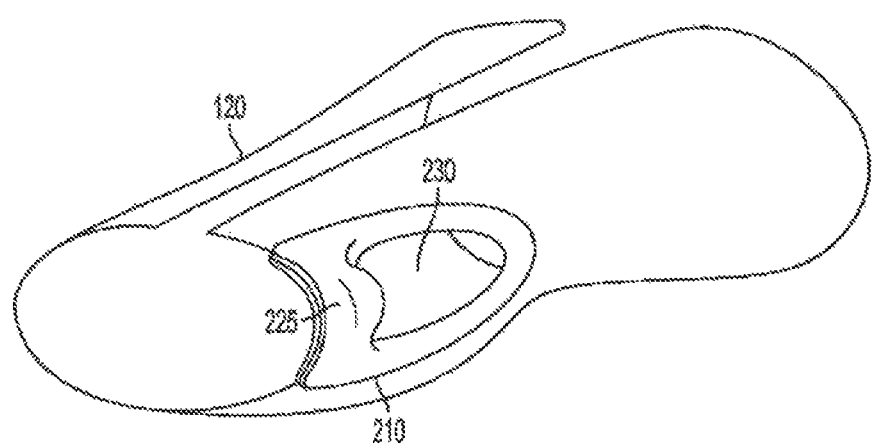
FIG. 2C shows another perspective view of a brace including the donut-shaped insert of FIG. 2A.

FIG. 2C shows a perspective view illustrating an example of the brace 120 with the donut insert 210 attached to the wrist brace 120.

Figure 3:
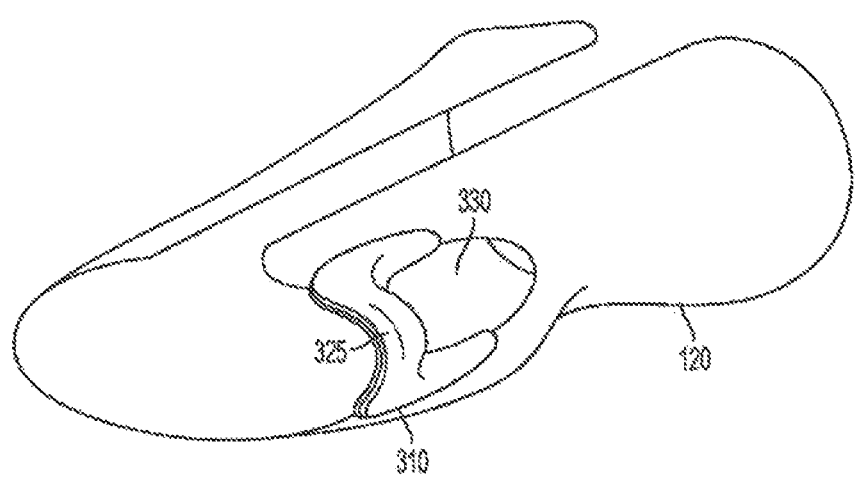
FIG. 3 shows a perspective view illustrating an example of a brace including a saddle insert.

FIG. 3 shows an example of the wrist brace 120 with a "saddle" insert 310. Saddle insert 310 spans the hand web space from the front of the hand to the back, between the thumb and the opposing fingers, but does not completely encircle the thumb, and attaches to only a portion of the thumbhole. Saddle insert 310 may include one or more contours, such as ridge 325, to provide additional cushioning and comfort.

Figures 4A, 4B:
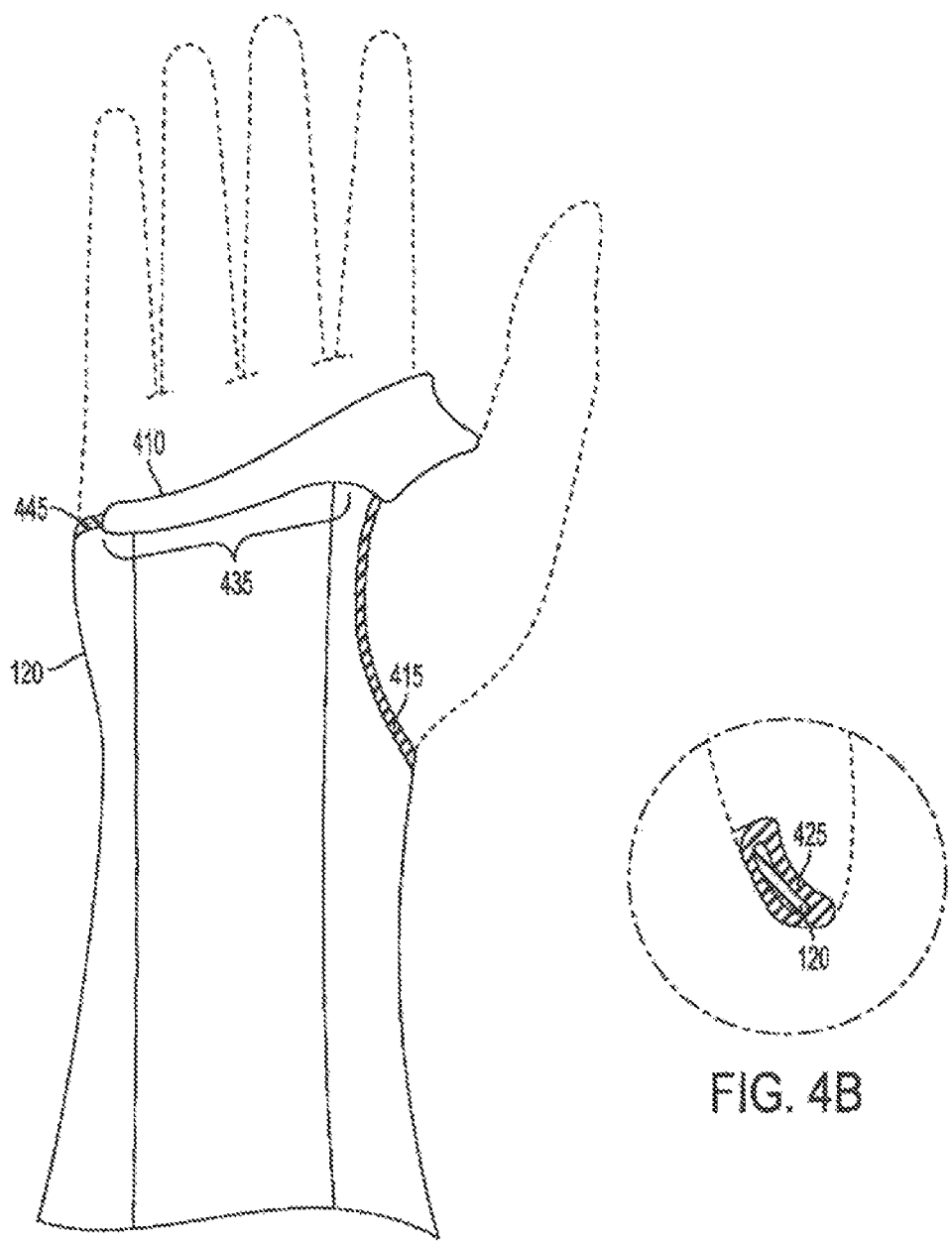
FIG. 4A shows a perspective view illustrating an example of a brace including a long saddle insert.
FIG. 4B shows a detail cross-section view of the insert of FIG. 4A.

FIG. 4A shows an example of the wrist brace 120 with a "long saddle" insert 410, which is a variation of the saddle insert 310 including a cushioned palmar extension 435 as an integral part of the long saddle insert 410. Palmar extension 435 provides padding comfort and protection across the palmar crease region of the hand where binding stitch-work 445 can irritate the skin, such as from rubbing.

FIG. 4B is a cross-section detail view illustrating an example of how the long saddle insert 410 may be contoured to conform to the curve of the web at the base of the thumb. The long saddle insert 410, like all other inserts (e.g., 110, 210, 310 and variations) may include contoured curved surfaces 425 to follow the line of the web space, and enable ease of thumb flexion.

Figure 5:
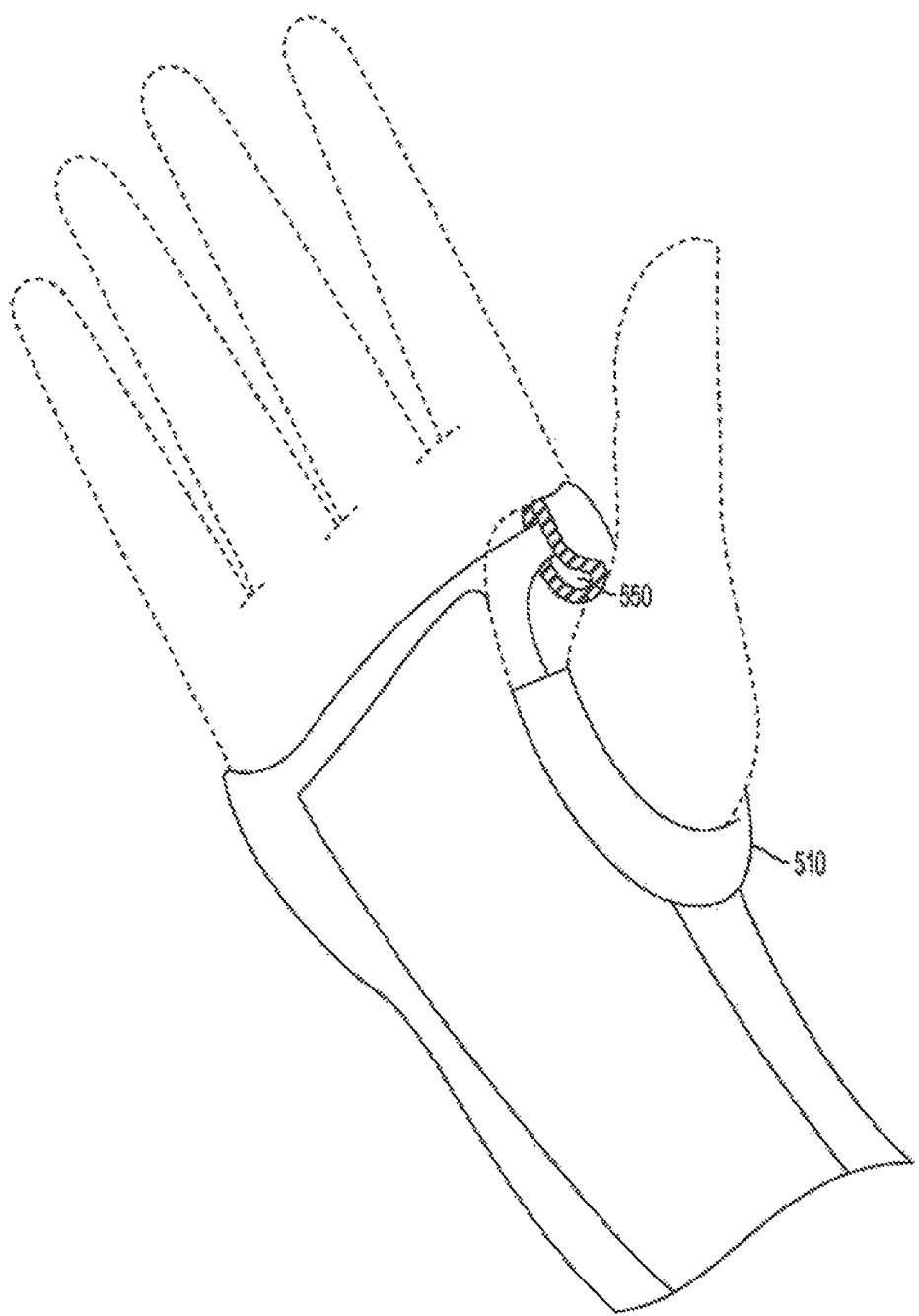
FIG. 5 shows a cut away perspective view illustrating an example of a donut insert including a hollow space.

FIG. 5 shows a cut-away view illustrating an example of a hollow donut insert 510 attached to the wrist brace 120. The hollow donut insert 510 is a variant of the donut insert 210 in that a hollow pocket space 550 is provided which can be filled with other materials to tailor the fit and firmness of the insert, as described below. The hollow pocket space 550 may be incorporated in any insert previously described and in any variants that may arise for custom requirements.

The insert can be made from a variety of materials, individually or in combination, where the key features include a combination of softness of feel for skin comfort, compression resistance for support, and breathability for air-flow and temperature comfort. Exemplary materials include foam compositions (e.g., open cell or closed cell), knit, woven/non-woven fabrics and felts. The fabric, in one embodiment, may be laminated to one or both sides of the foam to form a multilayered material, from which the insert is fabricated. Preferentially, the foam would have a soft feel to the touch and having a low coefficient of friction (COF) while providing an adequate amount of compression resistance for padding with support at the edges of the brace and in the web space and palmar crease area of the hand. In another embodiment, the insert may be a non-laminate, consisting of a foam material with no additional materials bonded to the foam, while providing a low coefficient of friction (COF) with an adequate amount of compression resistance for padding with support at the edges of the brace and in the web space and palmar crease area of the hand.

Figure 6:
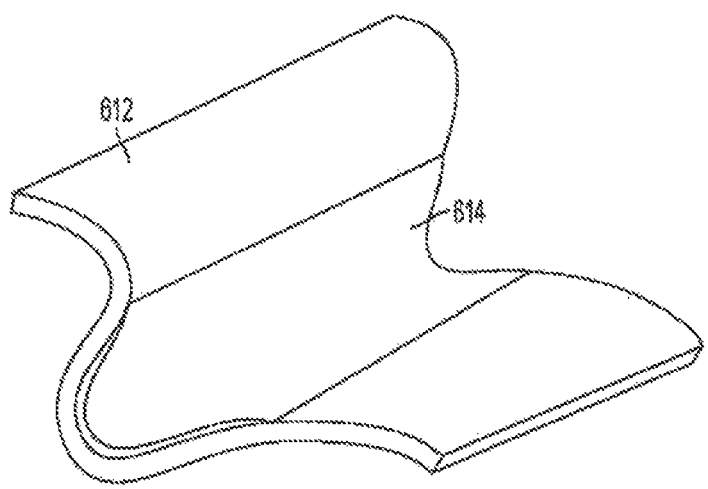
FIG. 6 shows a section view illustrating an example of an insert including compressible cushion material bonded to a portion of stretch-resistant material.

Lamination may be advantageous for various reasons. For example, when the foam is soft and stretchable, and may be subject to tearing under excessive use or strain, a lamination to a relatively stronger fabric with limited or no stretch ability can provide the added strength and stability to preserve an adequate service life of the insert. For example, FIG. 6 shows an example of a section or piece of insert 610 which include soft, stretchable foam 612 (or equivalent material) with at least a portion of one surface of the foam 612 laminated to a relatively non-stretch material 614 for strength. Insert 612 may be a pre-cut piece for later addition to a wrist brace 120, or may be integrally molded or shaped and manufactured with the brace 120.

Figure 7:
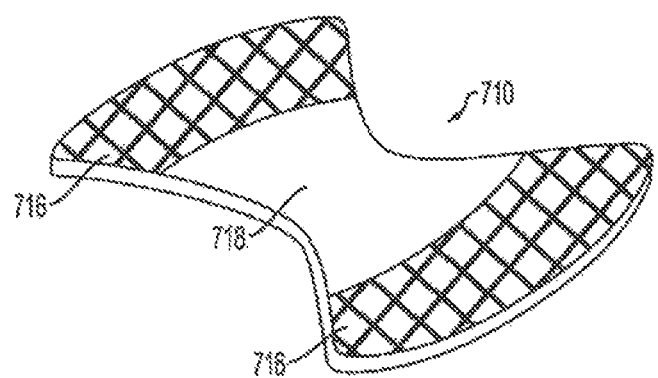
FIG. 7 shows a perspective view illustrating an example of a pre-cut insert including compressible cushion material and an adhesive layer.

FIG. 7 shows an example of a pre-cut insert 710, which includes foam, and further includes adhesive layers 716 laminated to foam 718 for attaching the pre-cut insert 710 to any wrist brace 120. Two separate areas of laminated adhesive are shown in FIG. 7 as one exemplary set of locations, but other configurations are possible and included within the scope of the invention. The adhesive layers 716 may attach directly to the brace 120 or, for example, by wrapping around the portion of the loop of the thumbhole 130 that crosses over the web area, and attach to each other. Various adhesive means may be used, including adhesive tapes, fabric hook and loop fasteners, such as Velcro™, heat welding, mechanical fasteners, glues, epoxies, hot melt glues, contact cement, heat and/or catalyst activated adhesive films, or other suitable securing means, and attachment may occur at various locations of the brace, according to the user's requirements. Mechanical fasteners may include sewing, hooks, buttons, etc., in which case material lamination may not be part of the adhesive system of attachment. Lamination of adhesives may be combined with lamination of other materials for differing mechanical purposes, and in the same or different portions of the insert.

Figure 8:
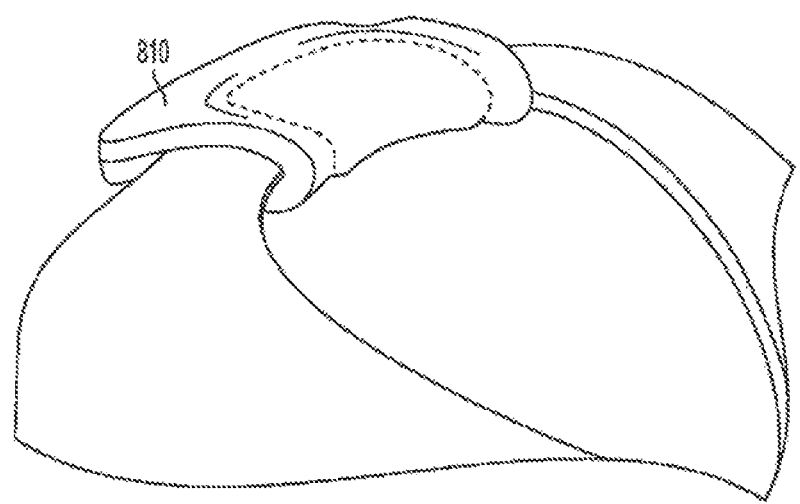
FIG. 8 shows a perspective view illustrating an example of an insert attached to a portion of the thumbhole of a brace, the insert containing a hollow portion.

FIG. 8 shows an example of a pocket insert 810, which is similar in function to the hollow donut insert 510. The pocket insert 810, as shown in one exemplary embodiment, as attached to the web portion of the thumbhole 130, includes a hollow space for incorporating a filler material for various purposes. For example, the filler may be a clay-like or wax-like material that molds to the shape of the hand and the brace at the contact surfaces to distribute contact force. Other filler materials may include foam beads, small solid beads (e.g., like a bean bag), and other materials with specific compressive and/or shaping properties, as required. Adhesive means, as discussed above, may be combined in the pocket insert 810 for attachment to the brace as well as to stabilize the location of the filler material within the pocket insert.

Figure 9:
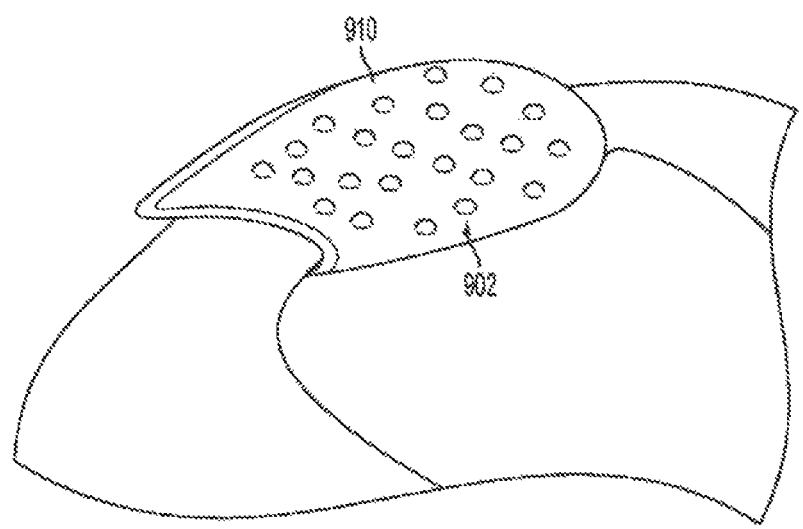
FIG. 9 shows a perspective view illustrating an example an insert attached to a portion of the thumbhole of a brace, the insert containing a pillow of foam beads in a hollow portion.

FIG. 9 shows an example of a "pillow" insert 910 attached to a portion of the loop of the thumbhole 130 of the brace 120, where the insert contains a pillow of foam beads in the hollow portion.

The exterior surface of the foam that comes in contact with the skin may further include a finish and texture that improves the contact "feel" and comfort by minimizing the coefficient of friction (COF) and may also enhance air flow to enable moisture release and reduce uncomfortable heat buildup at locations of skin contact with the brace 120. For example, the pillow insert 910 of FIG. 9 shows a textured surface 902 to enhance skin comfort. The textured surface 902 can be combined with any shaped insert.

Figure 10:
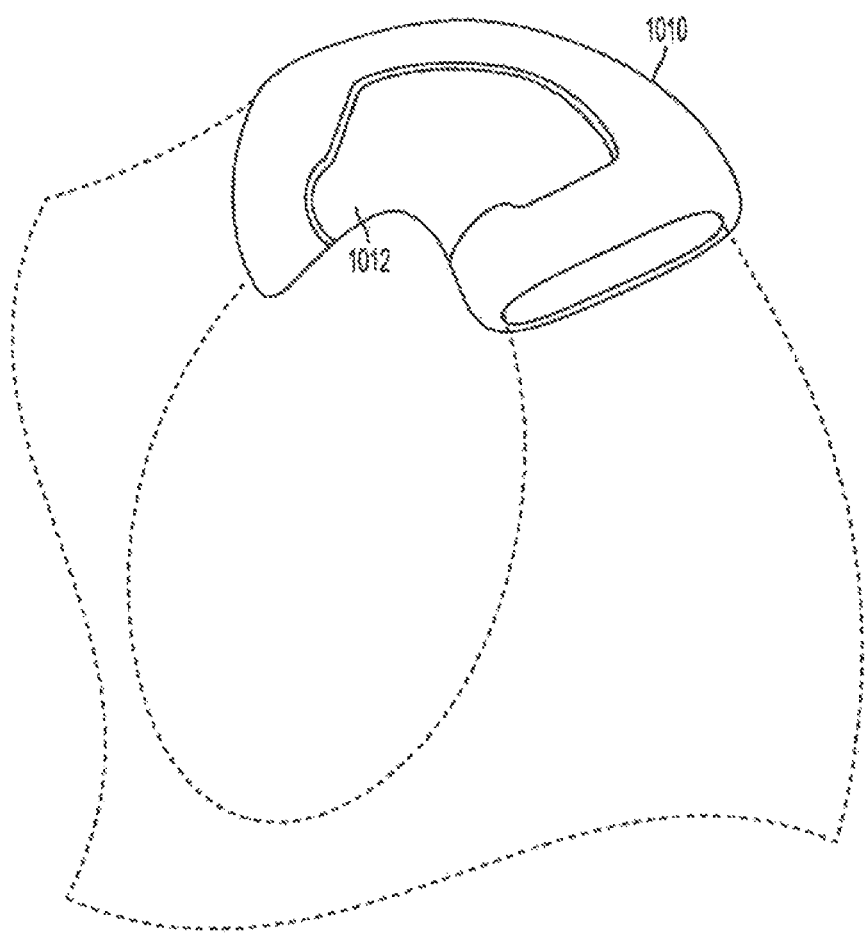
FIG. 10 shows a perspective view illustrating an example an insert attached to a portion of the thumbhole of a brace, the insert containing a recessed region for receiving an inlay.

FIG. 10 shows an example of an insert 1010 attached to a portion of the thumbhole 130 of a brace, the insert 1010 containing a recessed region 1012 for receiving an inlay of material having defined material characteristics depending on a user's requirements. The inlays may facilitate additional comfort or other functions. The inlays may be configured to cover selected areas where the skin makes contact with the brace insert. The inserts may comprise various materials such as, for example, foams having different density and/or compressibility, such as, for example, memory foam, slow recovery foam, cold-forming material that conformably shapes due to pressure and time to customize the shape of the insert to the user's anatomy for improved comfort and any material and/or surface texture that provides a defined feel.

Figure 11A:
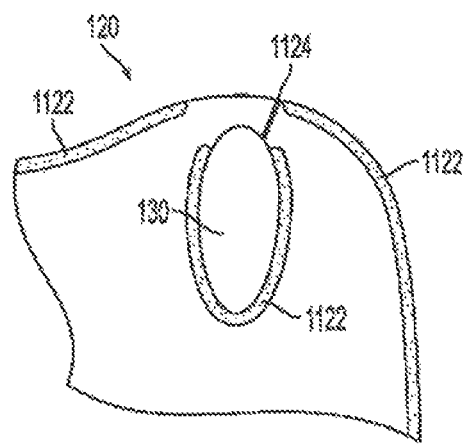
FIG. 11A shows a side view illustrating an example of a brace web space with a cut in the thumbhole for adding an insert.
Figure 11B:
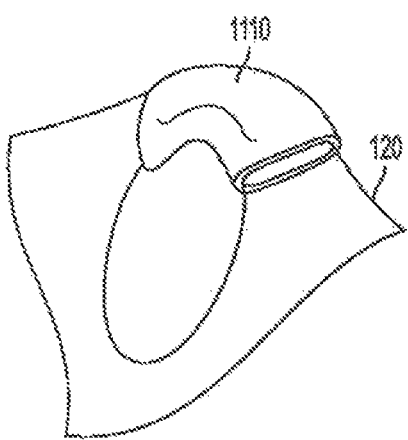
FIG. 11B shows a tube insert attached to a portion of the thumbhole of a brace in accordance with the disclosure.
Figure 11C:
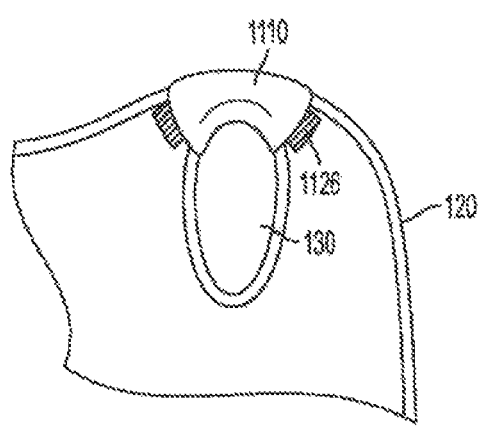
FIG. 11C shows a perspective view illustrating an example of brace web space with a tube insert over a reinforcement strip.

FIG. 11A shows an example of the web space of a brace with a cut in the thumbhole area for adding an insert to the brace. Stitch-work binding 1122 may extend along all or some edges of the brace 120. In the web space of the thumbhole 130 a cut 1124 can be made. FIG. 11B shows an example of a hollow "tube web insert" 1110 that may be inserted via the cut 1124 over the web space area of the brace 120. The tube web insert 1110 may be slid past the cut 1124 in order to sew or refasten the cut 1124. The tube web insert 1110 may be molded, extruded, or fabricated by other suitable means, either to a custom shape for a particular user, or to a generic shape. FIG. 11C shows an example of the tube web insert 1110 in place on the brace 120, where a reinforcement strip 1126 has been placed over the cut 1124 to refasten the ends of the cut 1124 together. Equivalent means may be used to achieve the same objective of refastening the ends of the cut 1124, including, but not limited to, fabric hook and loop fasteners, such as Velcro™, heat welding, mechanical fasteners, glues, epoxies, hot melt glues, contact cement, heat and/or catalyst activated adhesive films.

Figure 12:
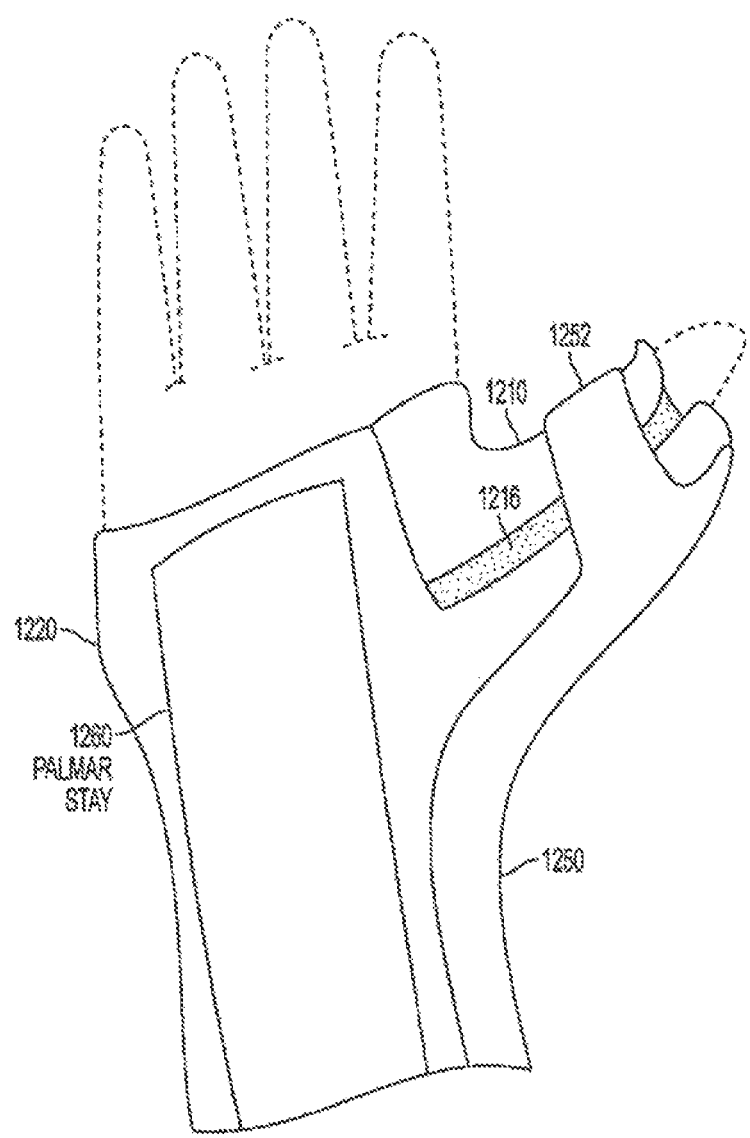
FIG. 12 shows a side view illustrating an example of an insert attached to an orthotic brace with a thumb stabilizer in accordance with the disclosure.

FIG. 12 shows an example of a thumb insert 1210 installed on a brace 120, and a thumb stay (splint) 1250 attached to a brace 1220 to immobilize a thumb. The brace 1220 may be substantially as described earlier, i.e., the brace 120 with the thumbhole 130 as shown in FIG. 1. Therefore, the insert may be partially outside the brace, especially in the web space area, and partially in direct contact with the thumb. Alternatively, the brace 1220 may be modified from brace 120 to expose a larger portion of the web space. Therefore, the thumb insert 1210 may be entirely in contact with the skin from the web space area of the hand to a substantial length along the side of the thumb facing the web space and a portion of the thumb. Attached to the thumb insert 1210 may be an elastic strip 1216 that may be used to attach to a part of the brace 1220 surrounding the outer side of the thumb, i.e., the side of the thumb that includes the thumb nail and faces away from the web space. The elastic strip 1216 may be sewn to the brace 1220, or alternatively attached by any of the attachment methods disclosed above, and their equivalents. The purpose of the elastic strip 1216, in addition to enabling a customized attachment of the thumb insert 1210 to the brace 1220 for comfort, is to provide a degree of flexibility and air flow breathability. The thumb insert is preferably inserted under a loop portion 1252 of the thumb stay 1250.

Figure 13A:
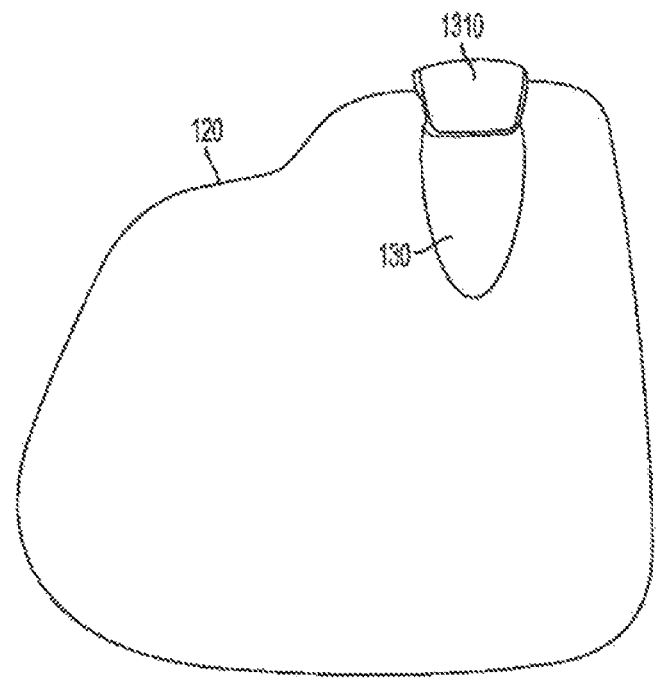
FIG. 13A shows a side view illustrating an example of a foam tape insert attached to a web region of an orthotic wrist brace.
Figure 13B:
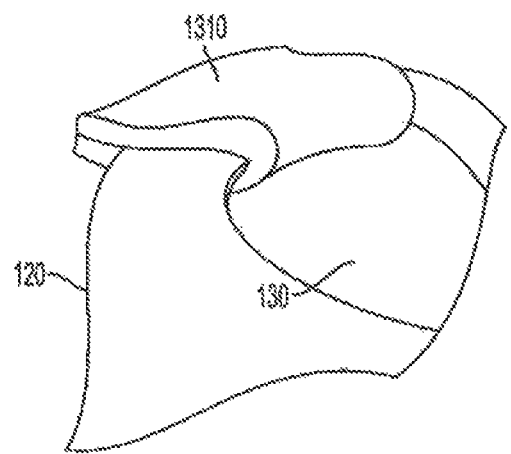
FIG. 13B is a detailed view FIG. 13A showing the foam tape attached to the web region of the orthotic wrist brace.

FIG. 13A shows an example of a foam tape insert 1310 attached to the brace 120 in the web space area of the loop that forms the thumbhole 130. The foam tape insert 1310 may preferably have an attachment means, such as a laminated adhesive layer on one surface, as described above, or equivalents. FIG. 13B shows a detail view illustrating an example of the foam tape insert 1310 attached to the brace using a self-adhering layer of adhesive. The foam tape insert 1310 may be cut to a required size and applied to the brace 120 at a location described above, or at any other location as required.

Figure 14A:
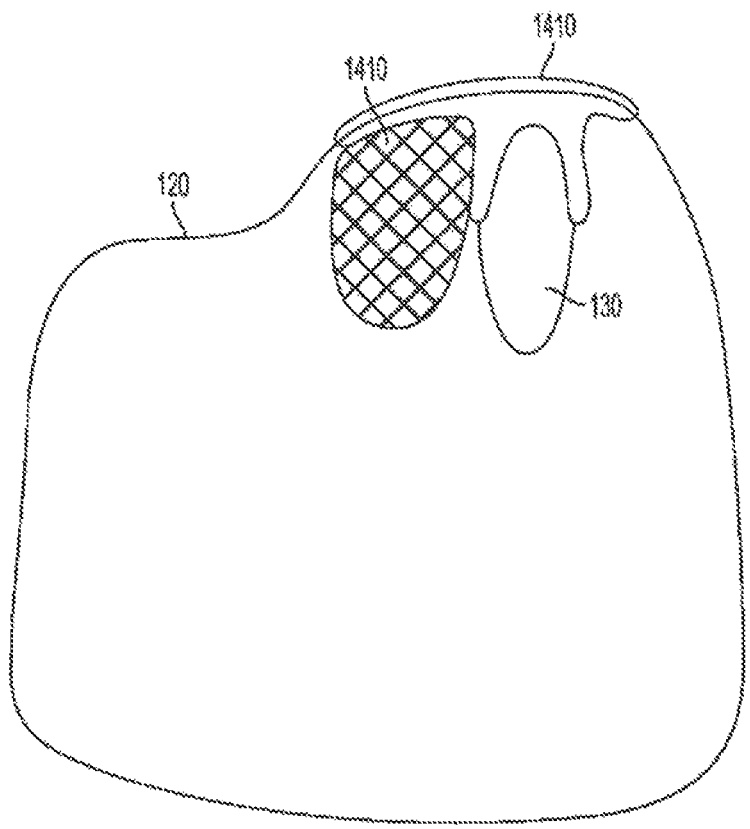
FIG. 14A shows a spacer pad insert attached to an interior surface of a brace in accordance with the disclosure.
Figure 14B:
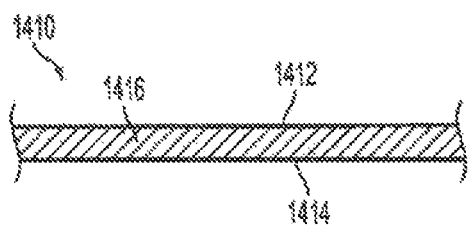
FIG. 14B shows a cross-section view illustrating an example of a spacer pad.
Figure 15:
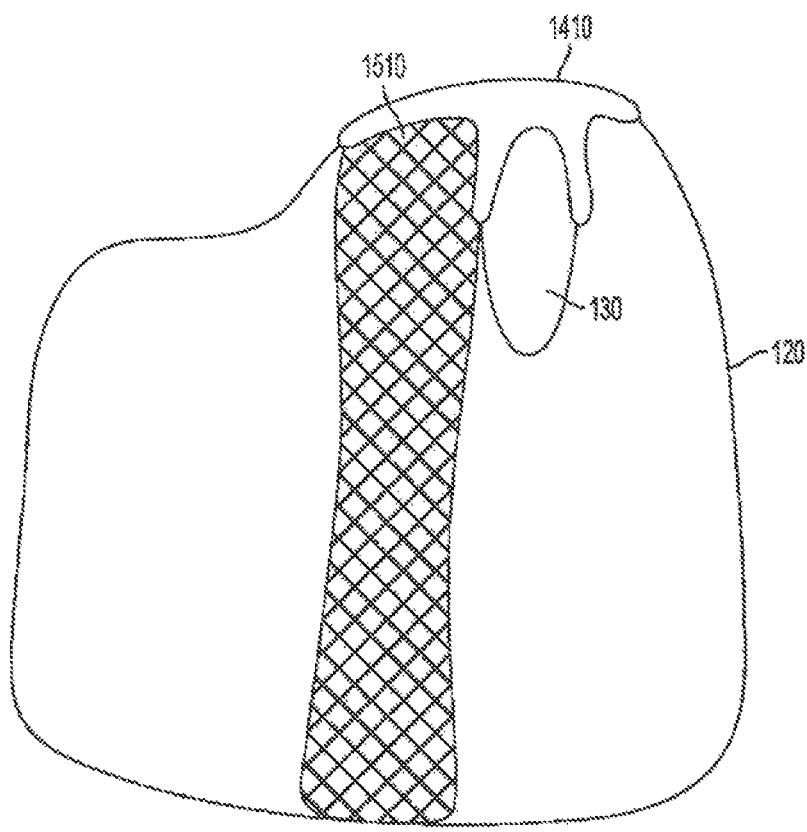
FIG. 15 shows a cross-section view illustrating an example of a long spacer pad located along the palmar stay region of an orthotic wrist brace.

FIG. 14A shows an example of a spacer pad insert 1410 attached to one of various interior surface locations of the brace 120. For reference, a long saddle insert 410 is also shown attached to the brace 120. FIG. 14B shows the spacer pad 1410 in cross-section. In one embodiment, the spacer pad insert 1410 comprises 3D knit materials, comprising two knit faces, i.e., a first knit face 1412 and a second knit face 1414 joined by a spacer yarn 1416. The three materials may be knit in a single process. The spacer yarn 1416 may provide improved comfort and coolness via cushioning and air breathability. As a further example, FIG. 15 shows a long spacer pad 1510 located along a palmar stay region of the orthotic wrist brace 120, attached using any of various adhesive means, as described above, including, at least, fabric hook and loop fasteners, such as Velcro™, a laminated contact adhesive layer, sewing, and the like.

Figure 16:
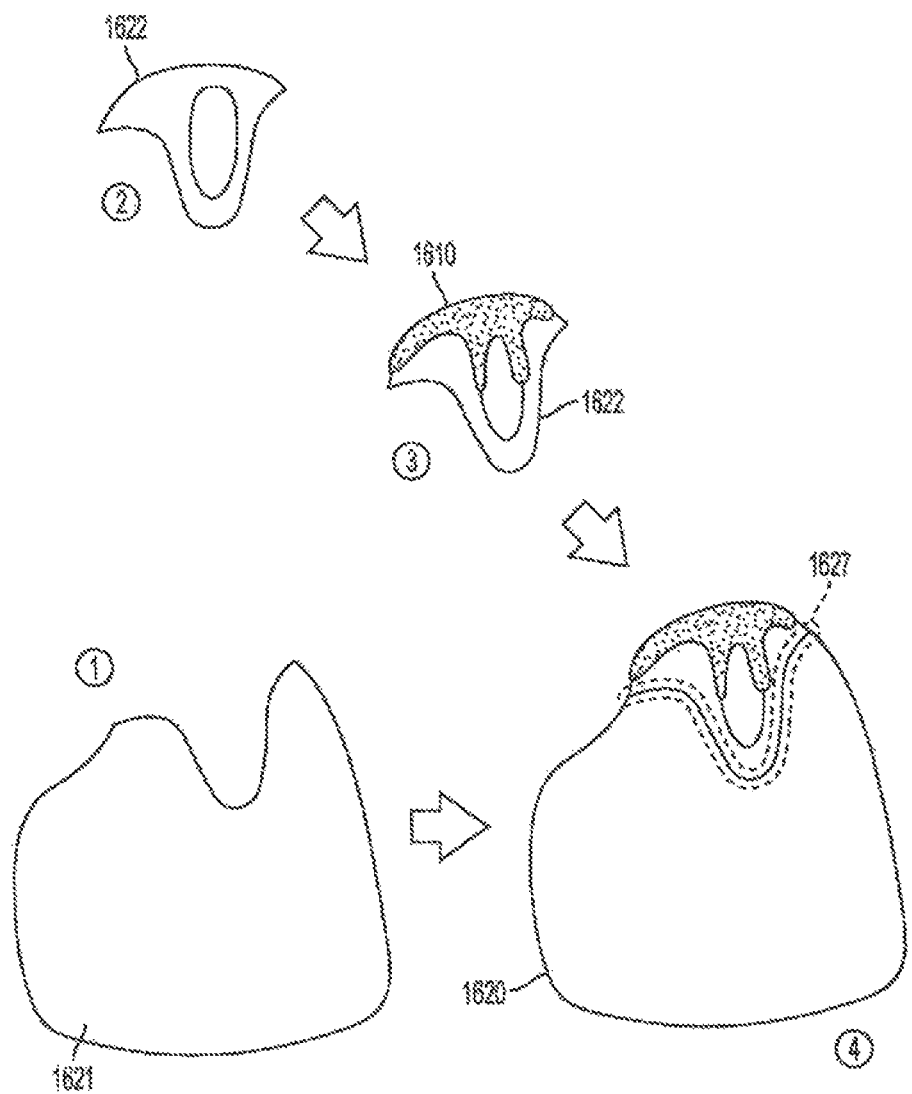
FIG. 16 illustrates an example of a method for making an orthotic wrist brace including a molded insert, a web area component and a main brace body part.

In one embodiment, a method of making a complete wrist brace 1620 with an integrally attached insert 1610 is shown in FIG. 16. A main body 1621 of the brace 1620 is fabricated (Step 1) to receive a second component 1622. Second component 1622 manufactured in Step 2, as shown for exemplary purposes, may be a component that surrounds the base of the thumb and may be shaped to receive an insert 1610 of particular type. Various types of inserts mentioned above include a donut, saddle, long saddle, and the like. Insert 1610 may be attached to second component 1622 (Step 3). Finally, the second component 1622, with insert 1610 already attached, is bonded (Step 4) to main body 1621 along a bonding interface 1627 by any of numerous attachment/bonding methods described above to form the complete wrist brace 1620.

In another embodiment, a method of making a wrist brace with an integrally attached spacer pad 1410 includes making a wrist brace 1620 and attaching the spacer pad 1410 to an interior surface of the brace 1620 at a defined location. The spacer pad 1410 may be cut or shaped as required and attached by any of the attachment means discussed above.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The various aspects of a flexible support presented throughout this disclosure are provided to enable one of ordinary skill in the art to practice the present invention. Various modifications to aspects presented throughout this disclosure will be readily apparent to those skilled in the art, and the concepts disclosed herein may be extended to other flexible supports. Thus, the claims are not intended to be limited to the various aspects of this disclosure, but are to be accorded the full scope consistent with the language of the claims. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A thumb brace, comprising:
   a brace configured to provide support to a user's wrist, the brace including a thumb hole;
   a thumb stay to immobilize the user's thumb when the thumb brace is worn by the user, the thumb stay including a loop member adapted to wrap around the user's thumb and a radial member extending from a user's wrist to the loop member; and
   a thumb insert inside the loop member and attached to the brace, the thumb insert having a first portion covering a portion of the brace and a second portion adapted to be in direct contact with a user's thumb while completely covering a webbing between the user's thumb and index finger, the insert attached along a strip located adjacent an outer region of the user's thumb wherein the brace comprises a first material and the thumb insert comprises a second material softer than the first material.

2. The thumb brace of claim 1 wherein the brace further comprises a palmer stay that is removably attached to the brace.

* * * * *